US008223921B2

(12) United States Patent
Makarov et al.

(10) Patent No.: US 8,223,921 B2
(45) Date of Patent: Jul. 17, 2012

(54) PIN BASE SENSOR FOR HIGH-THROUGHPUT MACROMOLECULAR CRYSTALLOGRAPHY

(75) Inventors: Oleg Makarov, Naperville, IL (US); Shenglan Xu, Darien, IL (US); Robert F. Fischetti, Plainfield, IL (US)

(73) Assignee: UChicagoArgonne, LLC, Chicago, IL (US)

( * ) Notice: Subject to any disclaimer, the term of this patent is extended or adjusted under 35 U.S.C. 154(b) by 294 days.

(21) Appl. No.: 12/793,961

(22) Filed: Jun. 4, 2010

(65) Prior Publication Data
US 2010/0322382 A1 Dec. 23, 2010

Related U.S. Application Data

(60) Provisional application No. 61/219,160, filed on Jun. 22, 2009.

(51) Int. Cl.
*G01N 23/207* (2006.01)

(52) U.S. Cl. ............................. 378/73; 378/81; 378/207
(58) Field of Classification Search .................. 378/73, 378/71, 207, 208
See application file for complete search history.

(56) References Cited

U.S. PATENT DOCUMENTS

| 5,629,524 A | 5/1997 | Stettner et al. |
| 6,057,552 A | 5/2000 | Stettner et al. |
| 7,712,960 B2 | 5/2010 | Sanishvili et al. |

*Primary Examiner* — Courtney Thomas
(74) *Attorney, Agent, or Firm* — Joan Pennington

(57) ABSTRACT

Sensing methods and a compact, sample holding pin base sensor are provided for detecting if a sample pin is, for example, properly mounted on a goniometer used for automated, high throughput macromolecular crystallography. A first magnet is used for holding a magnetic base; a second magnet is disposed spaced apart from the first magnet. The first magnet and the second magnet have opposite orientation. A Hall-effect switch is located generally centrally between the first magnet and the second magnet. A state of the Hall-effect switch indicates if a sample pin is properly mounted on a mounting member, such as a goniometer.

19 Claims, 2 Drawing Sheets

PIN BASE SENSOR FOR HIGH-THROUGHPUT MACROMOLECULAR CRYSTALLOGRAPHY

This application claims the benefit of U.S. Provisional Application No. 61/219,160 filed on Jun. 22, 2009.

CONTRACTUAL ORIGIN OF THE INVENTION

The United States Government has rights in this invention pursuant to Contract No. W-31-109-ENG-38 between the United States Government and The University of Chicago and/or pursuant to Contract No. DE-AC02-06CH11357 between the United States Government and UChicago Argonne, LLC representing Argonne National Laboratory.

FIELD OF THE INVENTION

The present invention generally relates to a sample holding pin used in automated, high throughput macromolecular crystallography.

More specifically, this invention relates to a compact, sample holding pin base sensor for detecting if a sample pin is properly mounted on a goniometer used for automated, high throughput macromolecular crystallography.

DESCRIPTION OF THE RELATED ART

In an automated system, such as, automated, high throughput macromolecular crystallography, a need exists for an effective mechanism for detecting if a sample pin is properly mounted on a goniometer. It is desirable to provide such mechanism that provides robust, accurate detection of the sample pin being properly mounted. It is desirable to provide such mechanism that overcomes disadvantages of laser-based sensing methods, and is not dependent upon ambient light conditions, light transmission or light reflection.

Principal objects of the present invention are to provide sensing methods and a compact, sample holding pin base sensor for detecting if a sample pin is properly mounted on a goniometer used for automated, high throughput macromolecular crystallography.

Important aspects of the present invention are to provide such methods and device substantially without negative effect and that overcome some of the disadvantages of prior art arrangements.

SUMMARY OF THE INVENTION

In brief, sensing methods and a compact, sample holding pin base sensor are provided for detecting if a sample pin is, for example, properly mounted on a goniometer used for automated, high throughput macromolecular crystallography. The sample holding pin base sensor includes a sample pin supported by a magnetic base. A first magnet is used for holding the magnetic base; a second magnet is disposed spaced apart from the first magnet. The first magnet and the second magnet have opposite orientation. A Hall-effect switch is located generally centrally between the first magnet and the second magnet. A state of the Hall-effect switch indicates if a sample pin is properly mounted on a mounting member, such as a goniometer.

In accordance with features of the invention, when the magnetic base is not mounted on the goniometer, there is no magnetic field in the middle point between the magnets, because the magnets have opposite orientation and magnetic field from the first magnet is cancelled by magnetic field from the second magnet. Then the Hall-effect switch is in an open state, which indicates the sample pin is not mounted on the goniometer. Otherwise, when the magnetic base is mounted on the goniometer, there is a magnetic field in the middle point between the magnets. Then the Hall-effect switch is in a closed state, which indicates the sample pin is properly mounted on the goniometer.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

In accordance with features of the invention, a sample holding pin base sensor is provided. The sample holding pin base sensor is used in an automated system, such as for high throughput crystallography automation. Goniometers are used, for example, for measuring angles between crystal faces in crystallography, and also are used in X-ray diffraction experiments to rotate the samples. The sample holding pin base sensor detects whether or not a sample is mounted on a corresponding mounting member or instrument, such as a goniometer.

In accordance with features of the invention, the assembly of the sample holding pin base sensor is based on commercially available pins used for crystal mounting and is compatible with all beamlines handling such samples.

In accordance with features of the invention, the sample holding pin base sensor detects whether or not a sample is mounted on the goniometer by sensing the state of a Hall-effect switch arranged in accordance with the preferred embodiment.

Figure 1:
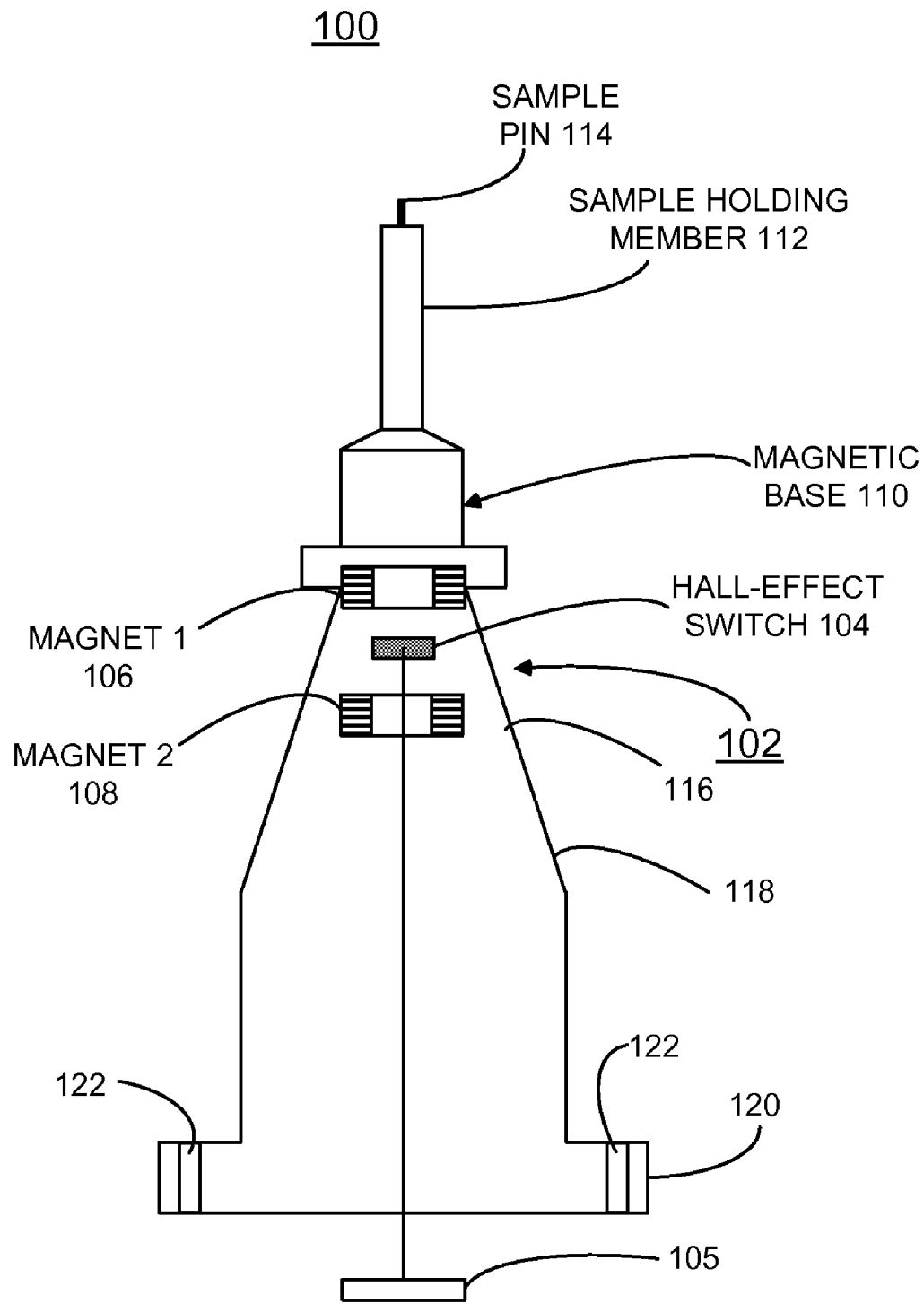
FIG. 1 is a schematic plan view of an exemplary sample holding pin base sensor for detecting if a sample pin is properly mounted on a goniometer and illustrating interior details in accordance with the preferred embodiment.

Having reference now to the drawings, in FIG. 1, there is shown an exemplary sample holding pin base sensor generally designated by the reference character 100 having capability for detecting whether or not a sample is mounted on a corresponding mounting member or instrument, such as a goniometer, in accordance with the preferred embodiment. Sample holding pin base sensor 100 advantageously is used for high throughput crystallography automation.

Sample holding pin base sensor 100 includes a sensor generally designated by the reference character 102. Sensor 102 includes a Hall-effect switch 104 including a testing connection member 105 for test system connection to detect a state of the Hall-effect switch 104. Hall-effect switch 104 is generally centrally located between a magnet 1, 106 and a magnet 2, 108. The magnet 1, 106 is used for holding a magnetic base 110; and the magnet 2, 108 is placed spaced apart from, behind the magnet 1, 106. The magnet 1, 106 and the magnet 2, 108 have opposite magnetic orientation.

Sample holding pin base sensor 100 includes the magnetic member or magnetic base 110 receiving the magnet 1, 106. Sample holding pin base sensor 100 includes a sample holding member 112, such as a sample holding pin 112, mounted on the magnetic base 110, used for sample mounting with a sample pin 114 holding a sample, for example, a protein micro crystal, disposed at an upper end of the sample holding pin base sensor 100.

For example, see U.S. Pat. No. 7,712,960, issued May 11, 2010 entitled "DEVICE FOR OPTIMIZATION OF EXPERIMENTAL PARAMETERS ON SYNCHROTRON BEAM LINES" to Ruslan Sanishvili, and Robert F. Fischetti, and assigned to the present assignee, discloses a device including an alignment pin with a needle for centering a rotation axis of the goniometer.

As shown, sample holding pin base sensor 100 includes a supporting member 116 engaging a mounting face of the magnetic member or magnetic base 110. The supporting member 116 contains the sensor 102, receiving and surrounding the Hall-effect switch 104, the magnet 1, 106 and the magnet 2, 108. The magnet 1, 106, and magnet 2, 108 are, for example, cylindrical disks or rings having approximately the same diameter. The supporting member 116 is an elongated member including a tapered portion 118, and a mounting base member or flange 120, at a distal end from the magnetic base 110. Sample holding pin base sensor 100 includes a plurality of apertures or holes 122 provided in the mounting flange 120 for removably mounting with a mounting member or instrument, such as the goniometer used in high throughput crystallography automation.

In operation of the sample holding pin base sensor 100, when the magnetic base is mounted on the goniometer, there is a magnetic field in the middle point between the magnet 1, 106, and magnet 2, 108. Then the Hall-effect switch 104 is in a closed state, which indicates the sample pin is properly mounted on the goniometer. Otherwise, when the magnetic base 110 is not mounted on the goniometer, there is no magnetic field in the middle point between the magnets, because the magnets have opposite orientation and magnetic field from the first magnet is cancelled by magnetic field from the second magnet. Then the Hall-effect switch is in an open state, which indicates the sample pin is not mounted on the goniometer.

The Hall-effect switch 104 is implemented with an integrated circuit, such as integrated circuit A3245LH manufactured and sold by Allegro Microsystems Inc., of Worcester, Mass. 01606, USA.

The sample holding pin base sensor 100 including the magnetic base 110, sample holding member 112 used for holding a sample with the sample pin 114 is based upon commercially available products used for crystal mounting and is therefore compatible with various beamlines handling such samples. The sample holding pin base sensor 100 is compatible for use with commercially available sample exchanger robotics, and can be applied at various facilities, which differ by the range of their operational parameters such as the sample-to-detector distance, monochromator energy range, maximum beam intensity and the like.

Figure 2:
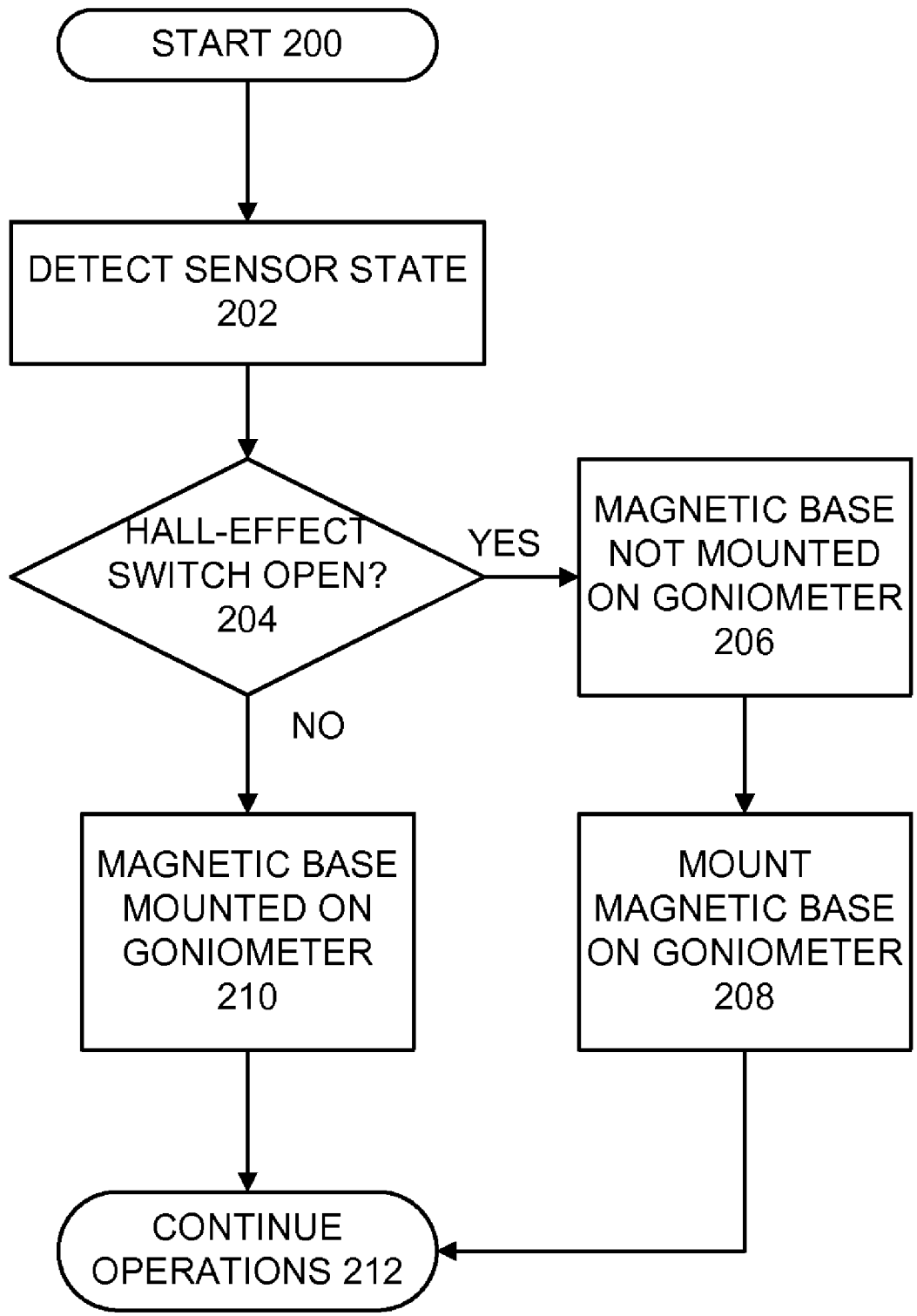
FIG. 2 is a flow chart illustrating exemplary steps for detecting if a sample pin is properly mounted on a goniometer with the sample holding pin base sensor of FIG. 1 in accordance with the preferred embodiment.

Referring now to FIG. 2, there are shown exemplary steps for detecting if a sample pin is properly mounted on a goniometer with the sample holding pin base sensor 100 in accordance with the preferred embodiment starting at a block 200. A sensor state of the sample holding pin base sensor 100 is detected as indicated at a block 202. Checking whether the Hall-effect switch 104 is open is performed as indicated at a decision block 204. When the Hall-effect switch 104 is open, then the magnetic base 110 is not mounted on the goniometer as indicated at a block 206. The magnetic base 110 is mounted on the goniometer as indicated at a block 208. When the Hall-effect switch 104 is closed, then the magnetic base 110 is mounted on the goniometer as indicated at a block 210. The operations continue as indicated at a block 212.

While the present invention has been described with reference to the details of the embodiments of the invention shown in the drawing, these details are not intended to limit the scope of the invention as claimed in the appended claims.

What is claimed is:

1. A sample holding pin base sensor for detecting a mounted sample pin comprising:
    a sample pin;
    a magnetic base supporting said sample pin;
    a mounting member for supporting said magnetic base;
    a first magnet for holding the magnetic base;
    a second magnet disposed spaced apart from said first magnet, said first magnet and said second magnet having an opposite orientation; and
    a Hall-effect switch provided between said first magnet and said second magnet; said Hall-effect switch having a state indicating the sample pin being mounted on said mounting member.

2. The sample holding pin base sensor as recited in claim 1 includes an alignment member for centering a goniometer rotation axis for automated crystallography.

3. The sample holding pin base sensor as recited in claim 1 wherein said Hall-effect switch is generally centrally located between said first magnet and said second magnet.

4. The sample holding pin base sensor as recited in claim 1 wherein said mounting member includes a goniometer.

5. The sample holding pin base sensor as recited in claim 1 wherein said Hall-effect switch has an open state indicating the sample pin is not mounted on said mounting member.

6. The sample holding pin base sensor as recited in claim 1 wherein said Hall-effect switch has a closed state indicating the sample pin is mounted on said mounting member.

7. The sample holding pin base sensor as recited in claim 1 includes a supporting member engaging a mounting face of the magnetic base.

8. The sample holding pin base sensor as recited in claim 7 wherein said supporting member receives said Hall-effect switch, said first magnet, and said second magnet.

9. The sample holding pin base sensor as recited in claim 1 wherein said supporting member is mounted to a goniometer.

10. The sample holding pin base sensor as recited in claim 1 wherein said magnetic base supports an alignment member for aligning with an X-ray beam at a sample position.

11. A method for detecting a mounted sample pin with a sample holding pin base sensor, said method comprising the steps of:
    providing a magnetic base supporting a sample pin;
    providing a mounting member for supporting said magnetic base;
    providing a first magnet for holding the magnetic base and a second magnet disposed spaced apart from said first magnet, said first magnet and said second magnet having an opposite orientation;
    providing a Hall-effect switch between said first magnet and said second magnet; and
    detecting a state of said Hall-effect switch, said state indicating whether the sample pin being mounted on said mounting member.

12. The method as recited in claim 11 includes providing an alignment member for centering a goniometer rotation axis for automated crystallography.

13. The method as recited in claim 11 includes providing said Hall-effect switch generally centrally located between said first magnet and said second magnet.

14. The method as recited in claim 11 wherein said Hall-effect switch has an open state indicating the sample pin is not mounted on said mounting member.

15. The method as recited in claim 11 wherein said Hall-effect switch has a closed state indicating the sample pin is mounted on said mounting member.

16. The method as recited in claim 11 wherein said mounting member includes a goniometer.

17. The method as recited in claim 11 includes providing a supporting member engaging a mounting face of the magnetic base.

18. The method as recited in claim 17 wherein said supporting member receives said Hall-effect switch, said first magnet, and said second magnet.

19. The method as recited in claim 11 wherein said supporting member is mounted to a goniometer.

* * * * *